United States Patent [19]

Magny et al.

[11] 4,035,517

[45] July 12, 1977

[54] PROCESS FOR TREATING THE RESIDUE FROM THE DISTILLATION OF WHITE WINE

[75] Inventors: Jean Magny; Charles Montant; Pierre Raynaud, all of Toulouse; Charles Gontier, Colomiers; Jacques Dardenne, Toulouse, all of France

[73] Assignee: E. Remy Martin & Co., Cognac, France

[21] Appl. No.: 593,983

[22] Filed: July 8, 1975

Related U.S. Application Data

[63] Continuation-in-part of Ser. No. 503,679, Sept. 6, 1974, abandoned.

[30] Foreign Application Priority Data

Sept. 6, 1973   France .............................. 73.32213

[51] Int. Cl.² ......................................... A23L 1/28
[52] U.S. Cl. ................................... 426/31; 426/53; 426/54; 426/60; 195/81

[58] Field of Search ................ 426/60, 61, 31, 624, 426/3, 53, 54; 195/4, 5, 29, 13, 32, 35, 105, 106

[56] References Cited

U.S. PATENT DOCUMENTS

2,595,827   5/1952   Boruff et al. .................... 426/31 X

FOREIGN PATENT DOCUMENTS

1,095,274   5/1955   France
1,078,133   12/1954  France

*Primary Examiner*—Raymond N. Jones
*Assistant Examiner*—Esther L. Massung
*Attorney, Agent, or Firm*—Brisebois & Kruger

[57] ABSTRACT

Yeast-containing sludge is separated from residue produced by the distillation of white wine and the remaining residue is innoculated with fungus culture, e.g. a penicillium, the resulting biomass removed, and the remaining residue purified and used in animal feed.

7 Claims, 1 Drawing Figure

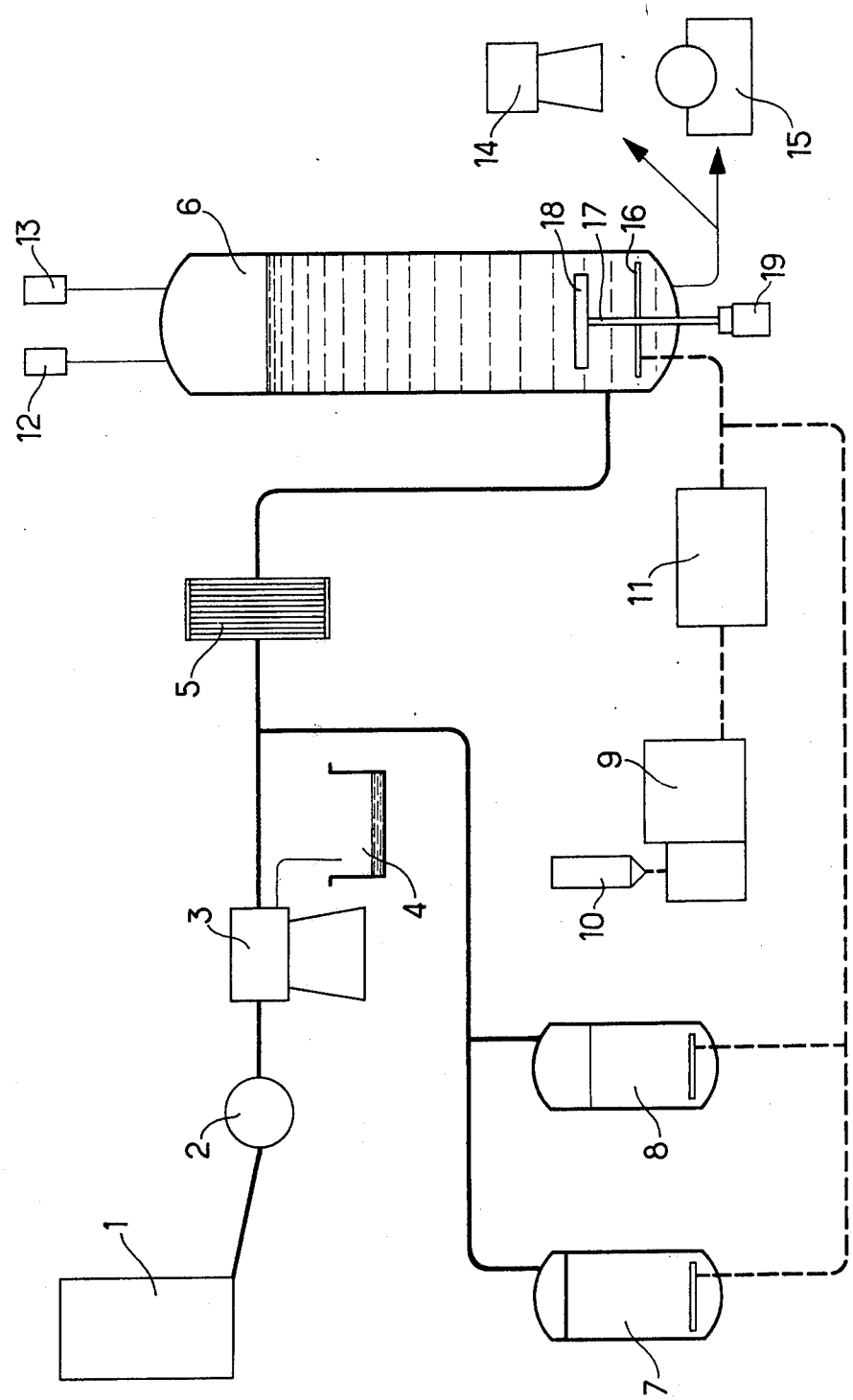

PROCESS FOR TREATING THE RESIDUE FROM THE DISTILLATION OF WHITE WINE

This application is a continuation in part of application Ser. No. 503,679, filed Sept. 6, 1974 now abandoned.

SUMMARY OF THE INVENTION

This invention relates to a process for treating the residues resulting from the distillation of white wine by utilizing selected micro-organisms as well as by recovery of the biomass produced thereby for use as a source of nutrients.

It is well known that the residues from the distillation of white wine have a very polluting effect, both by reason of their physical properties and their high temperatures of more than 80° C, their low pH of the order of 3.3, the presence of a substantial amount of material in suspension, and their undesirable odor, as well as by reason of their chemical properties with respect to the low content of dissolved oxygen, the high chemical demand for oxygen which is in the neighborhood of 40,000 mg of oxygen/liter, the high biochemical demand for oxygen which is in the neighborhood of 30,000 mg of oxygen/liter, and the presence of organic and mineral materials in solution.

These residues have been heretofore practically unusable because the only product recovered from treating them has been tartaric acid. Moreover, the production of tartaric acid by chemical synthesis has become a highly competitive method so that the commercial utility of even this utilization of white wine residues has decreased.

The residue has been used as fertilizer to supplement the organic materials in the soil and spread among the vines.

The residue from the first distillation, which represents about two-thirds of the volume of wine treated in the still, is very rich in organic material in suspension, such as raisin pulp, wine making yeast, and various wastes, and materials in solution such as carbohydrates and various nitrogenous compounds.

The discharge of such polluting residues into the environment poses problems for distilleries, which are then subjected to heavy taxes.

Applicant has now discovered in a surprising fashion that the residue of the first distillation of the distillation of white wines may constitute a choice medium for the culture of certain micro-organisms rich in nitrogenous materials and which may be effectively used as nitrogenous supplements to the feed for various animals, and that this process results in a reduction of at least 30% in the quantity of these highly polluting residues which must be disposed of.

In effect, the residues from the distillation of white wines are rich in carbonaceous and nitrogenous materials. As a consequence of chemical analysis and culture tests in the laboratory applicant has found that such a medium in no way inhibits growth of such micro-organisms. Moreover, the applicant has found that the yeasts which contain an average of about 32% protein which may be recovered after each removal of yeast from the residue are entirely suitable for use in animal feeds for such animals as rabbits, calves, etc. The growth and development of groups of animals fed a ration containing this yeast was at least comparable to that of test animals fed a commercial animal feed. Thus the yeast constituted an important protein contribution to the feed for the animals and had no toxic effect on them.

Moreover, the low tannin content of white wines, in particular those wines used for the production of Cognac, is an important factor which makes it possible to use the treated residues from wine making for the feeding of animals without incurring the least risk.

The present invention relates to a process for treating the residues from the distillation of white wines characterized by the fact that it consists in centrifugally separating the sludge containing the wine making yeasts from the raisin pulp, cooling the medium from which the yeast has been removed and innoculating it with a preculture formed itself in the same medium, for example by the suspension of lyophilized spores, leaving the micro-organism to develop, separating and recovering the biomass produced from the culture medium, and treating the liquid medium with a view to high purification.

In order to carry out the present invention it is possible to use any of the residues produced by the fermentation of white wine. For example, after removing the yeast from the residue produced from the distillation of Cognac wines, the liquid has the following average composition per 1000 g of water:

| | | |
|---|---|---|
| Total dry matter | 25 | g |
| Total mineral material | 3 | g |
| Total organic material | 22 | g |
| Total nitrogenous material | 376 | mg |
| Reducing sugar | 1,089 | mg |
| Total sugar | 1,280 | mg |
| Total organic acidity | 160 | milliequivalents |
| Amino acids | 850 | mg |
| Chemical demand for oxygen | 35,000 | mg of oxygen/liter |
| Biochemical demand for oxygen | 23,000 | mg of oxygen/liter |

S = 42 mg

P = 104 mg

Ca = 198 mg

Mg = 85 mg

K = 808 mg

Na = 6 mg

Fe = 32 mg

Mn = 2 mg

Cu = 6 mg

Zn = 3 mg

These residues may be enriched with carbonaceous or nitrogenous constituents, mineral vitamins, or mixtures thereof as circumstances demand. Nitrogen, for example, may be supplied by adding an ammonium salt, urea, blood meal, soluble fish products, etc.

In accordance with the present invention the process comprises the growth of a micro-organism belonging to the fungi group which, by its specific growth on the residue from the distillation of white wines, produces a biomass of at least 4 g/liter containing at least 20% protein. The resulting depollution is proportional to the production of fungi and is greater when this production is greater. The cultures selected and capable of suitably developing on the residues from the distillation of white wine may belong to any species of actinomycetes and fungi (including yeasts): Actinomycetes, Ascomycetes, Siphomycetes, Septomycetes, as they are classified in general works such, for example, as LECHEVALIER and PRAMER, "The Microbes" printed by Lippincott in Philadelphia, U.S.A., in 1971, and ALEXOPOULOS, "Introductory Mycology", 2nd edition, printed by Wiley in New York, and, of course, more specialized works in the mycological literature.

The present invention is not limited to any particular species of fungi.

However, the following micro-organisms may be listed as preferred:

Penicillium Spinulosum Thom, strain 129
Penicillium Expansum Link, strain 127
Penicillium Commune Thom, strain 125

These three newly discovered penicillium are obtained by isolating them from stagnant vinasse found in the area of Cognac, France. The characteristics of the penicillium are as follows:

Penicillium Commune Thom (ATCC 20464)

Taxonomic characteristics:

Class: Fungi imperfecti
S/Class: Hyphomycetes
Order: Mucedineae
Family: Mucedinaceae
S/Family: Aspergilleae
Genus: PENICILLIUM Cultural characteristics:

The lanuginous colonies on a Czapek agar medium attain at the end of 10–12 days a diameter of 3–4 cm at 25° C.
— White edge, then gray, 2 cm in width.
— Colorless exudate mixed with the mass of mycelium.
— Strong musty odor.
— Other side colorless.

Microscopic characteristics:
- Conidiophores: $L = 500\mu$  $l = 5\mu$
  - finely ornamented wall in the young cultures which becomes rougher with age.
- Hairs: $L = 40 - 50\mu$, Asymetric
  - Ramifications and metulae attaining different levels.
  - Ramifications: $L = 15 - 20\mu$
  - Metulae: $L = 15 - 20\mu$  $l = 3 - 3.5\mu$
  - Sterigma: $L = 10 - 12\mu$  $l = 3\mu$
  - Conidia in smooth ellipitic chains $(4 = 5\mu)$.

Penicillium Expansum Link (ATCC 20466)

Taxonomic characteristics:

Class: Fungi imperfecti
S/Class: Hyphomycetes
Order: Mucedineae
Family: Mucedinaceae
S/Family: Aspergilleae
Genus: PENICILLIUM
Cultural characteristics:

On a Czapek agar medium the colonies attain a diameter of 4–5 cm at the end of 8 days of culture at the ambient temperature (25° C).
— Radial grooves, 0.5–2 cm deep.
— White edge, 1–2 cm wide, white at the beginning of growth turning yellow-green at the moment of sporulation.
— Few exudates in the form of colorless drops imprisoned in the mass of mycelium.
— Strong musty odor, characteristic of rotten apples.
— Other side colorless.

Microscopic characteristics:
- Conidiophores: Grouped in bundles, walls smooth or finely ornamented.
  - $L = 150 - 400\mu$
  - $l = 3 - 3.5\mu$
- Hairs: - Asymetric $L = 75 - 100\mu$
  - Presence of 1 or 2 ramifications.
  - Ramifications: $L = 15 - 25\mu$
    $L = 2.5 - 3.5\mu$
  - Metulae arranged in whorls.
    $L = 10 - 15\mu$
    $l = 2.2 - 3\mu$
  - Sterigma in groups of 5 – 9.
    $L = 8 - 12\mu$
    $l = 2 - 3.5\mu$
  - Conidia in smooth elliptic chains $(3 \times 3.5\mu)$.

Penicillium Spinulosum Thom (ATCC 20465)

Taxonomic characteristics:

Class: Fungi imperfecti
S/Class: Hyphomycetes
Order: Mucedineae
Family: Mucedinaceae
S/Family: Aspergilleae
Genus: PENICILLIUM Cultural characteristics:

The colonies on a Czapek agar medium attain at the end of 12–14 days a diameter of 4.5–5.5 cm at 25° C.
— No exudates.
— Very slight odor.
— Bottom side almost colorless.

Microscopic characteristics:
- Conidiophores: Emerging directly from the substrate
  $L = 100 - 200\mu$
  - Emerging from raised hypha.
    $L = 25 - 50\mu$
  - Always smooth, and have an anterior vesicule in which $\phi = 5\mu$ carrying the hairs.
- Hairs: - type Monoverticillate
  - Sterigma: 6 – 10 positioned vertically.
    $L = 6 - 9\mu$
    $l = 2.2 - 3.3\mu$
  - Conidia in echinulate chains which are elliptical or subglobular $(3 \times 3.5\mu)$ Also preferred are the following micro-organisms above-listed:

Penicillium Commune Thom, strain 148
Penicillium Expansum Link, strain 118
Penicillium Frequentans Westl, strain 142

These three newly discovered penicillium have the characteristics as follows:

Pencillium Commune Thom (ATCC 20469)

Taxonomic characteristics:

Class: Fungi imperfecti
S/Class: Hyphomycetes
Order: Mucedinae
Family: Mucedinaceae S/Family: Aspergillae
Genus: PENICILLIUM
Structure: Asymmetrical; no divaricated; Lanata
Species: COMMUNE Morphological characteristics:

The colonies on a Czapek medium attain at the end of 10–12 days of culture at 25° C a diameter of 3–4 cm
— Lanuginous mass of mycelium (500 to 700 $\mu$)
— White edge (2 mm) turning gray at the end of growth
— Colorless exudate mixed with the mass of mycelium
— Other side colorless
— Strong musty odor.

---

Microscopic characteristics:
- Conidiophores : finely ornamented wall in the young cultures, very ornamented wall in the aged cultures
  L = 400 – 500$\mu$
  l = 5$\mu$
- Hairs :
  - Asymetric
  - Ramifications and metulae attaining different levels
  - Metulea : L = 15 – 20$\mu$   l = 3 – 3.5$\mu$
  - Sterigma: L = 10 – 12$\mu$   l = 3 – 3.5$\mu$
  - Conidia in smooth elliptic chains (4 × 5$\mu$)

---

Penicillium Expansum Link (ATCC 20467)

Taxonomic characteristics:

Class: Fungi imperfecti
S/Class: Hyphomycetes
Order: Mucedinae
Family: Mucedinaceae
S/Family: Aspergillae
Genus: PENICILLIUM
Structure: Asymmetrical; no divaricated; fasciculata
Species: EXPANSUM Morphological characteristics:

The colonies on a Czapek medium attain a diameter of 4–5 cm at the end of 8 days of culture at 25° C.
— Radial grooves, 0.5–2 cm deep
— White edge, white at the beginning of grooth, turning yellow-green at the moment of sporulation
— Few exudates in the form of colorless drops
— Other side colorless
— Strong musty odor, characteristic of rotten apples.

---

Microscopic characteristics
- Conidiophores : Grouped in bundles, walls smooth or finely ornamented.
  L = 150 – 400$\mu$
  l = 3 – 5$\mu$
- Hairs :
  - Asymetric with 1 or 2 ramifications
    L = 15 – 25$\mu$
    l = 2.5 – 3.5$\mu$
  - Metulae arranged in 3 whorls
    L = 10 – 15$\mu$
    l = 2.2 – 3$\mu$
  - Sterigma in groups of 5 – 9
    L = 8 – 12$\mu$
    l = 2 – 2.5$\mu$
  - Conidia in chain 150 – 200$\mu$ long
  - smooth
  - elliptic (3 – 3.5$\mu$

---

Penicillium Frequentans Westl (ATCC 20468)

Taxonomic characteristics:

Class: Fungi imperfecti
S/Class: Hyphomycetes
Order: Mucedinae
Family: Mucedinaceae
S/Family: Aspergillae
Genus: PENICILLIUM
Structure: Monoverticillata strict; no peritheci; no sclerote
Species: FREQUENTANS Morphogical characteristics:

The colonies on a Czapek medium attain a diameter of 3–6 cm at the end of 10–12 days of culture at 25° C.
Broad, wrinkled zonations;
Few exudates, amber coloured;
Slight musty odor;
Other side yellow-orange sometimes brown-purple.

---

Microscopic characteristics :
- Conidiophores : walls smooth or finely ornamented ends of conidiophore extended (5 $\mu$)
  L = 100 – 200 $\mu$   l = 3.0 – 3.5 $\mu$
Hairs :
  - Monoverticillate strict
  - Sterigma : 10 – 12 positioned vertically
    L = 8 – 12 $\mu$   l = 3.0 – 3.5 $\mu$
- Conidia in chains (150$\mu$), globular, smooth walls,
  $\phi$ = 3.0 – 3.5 $\mu$

---

The numbers after "ATCC" indicate the accession numbers at Amercian Type Culture Collection in Rockville-Maryland U.S.A.

These micro-organisms have been deposited with the American Type Culture Collection, 12301 Parklawn Drive, Rockville, Maryland, 20852, and they have the following ATCC numbers:

Pencillium commune (strain 125), ATCC 20464
Pencillium spinulosum (strain 129), ATCC 20465
Pencillium expansum (strain 127), ATCC 20466.
Pencillium expansum (strain 118) ATCC 20467
Pencillium frequentans (strain 142) ATCC 20468
Pencillium commune (strain 148) ATCC 20469

Among the tested strains, the above identified strains of Penicillium were retained because of their characteristics as follows:
—good adaptation for the culture medium: residues from the distillation of white wines.
—good growth at a low pH
—better exhaustion of the medium.

In accordance with the present invention, the choice of such microorganisms results in a greater resulting depollution, i.e. a lower chemical demand for oxygen and a lower biochemical demand for oxygen, as well as in a higher yield as regards the dry weight of the produced biomass and the culture time which is shorter. Moreover, the proteins content of biomass is more important and the results for an animal feed are better.

The culture of the micro-organisms may be effected either continuously or discontinuously. However, regardless of the system envisaged, the medium must be acidified and maintained at a pH of 1.5–5, and preferably 1.5–3. Indeed, Applicant has discovered in a surprising fashion that a low pH value is favourable to decrease the bacterial contamination. Moreover, such a low pH is selected to avoid modifying too much the natural pH of the residues from the distillation of white wines, which is near 3.2. An automatic system indicates the formation of foam. The agitation and aeration of the medium are kept up throughout the culture period. These two parameters are very important and are, like the time factor, a function of the micro-organism used as well as the maximum degree of depollution which may be obtained, for example, a biochemical demand for oxygen of 6,500 mg/liter, and also the biosyntheses observed, such as those of proteins and amino acids. For example, the aeration may be ranging between 1/3 and 1/2 1/min./1 - medium.

The quantity of the biomass produced is at least 4 g/liter and may reach 10 g/liter. This biomass consists of at least 20% protein.

After separating the biomass the filtrate is still treated first through a diatomaceous filter to remove the fine particles in suspension and then by reverse osmosis. Also, the reverse osmosis may be replaced by a conventionnal concentration carried out in an evaporator. Such a treatment results in a complete depollution of the liquid (less than 40 mg of oxygen/liter) conforming to legislative requirements and in the obtaining a concentrated liquid from which the bio-synthesized molecules are collected. These molecules consist mainly of amino acids, such as aspartic acid, glutamic acid, proline, alanine, lysine, arginine and asparagine. They may be incorporated into animal feed, but also into pharmaceutical compositions.

The invention may be better understood from a study of a representative embodiment of a device for treating the material in accordance with the invention illustrated on the single figure of drawings, which is a flow sheet for a representative process.

In the illustrated embodiment the residue coming from the still 1 is delivered by a pump 2, to a centrifugal separator 3 and thence through a heat exchanger 5 to the fermenter 6. The centrifugal separator 3, which may be of the ALFA-LAVAL type, equipped with automatic washing means which works during operation, separates out the sludge in suspension in the liquid. This is collected in a simple tank 4 made of plastic material. The heat exchanger 5 is used as a coller and must bring the liquid to a temperature of about 40° C in the ducts and the polyvinyl chloride fermenter. Two stainless steel containers 7, 8 are used for the preculture and the preparation of nutritive solutions. They are stationary and are directly connected to air and steam lines (not shown) as well as to the culture medium through a pump (not shown). The fermenter 6, having a total capacity of 10 cubic meters, serves for the culture of the organisms and is provided at its lower end with a perforated ring 16 for the admission of air and preferably with a shaft 17 provided with blades 18 driven by an electric motor 19 in order to agitate the medium. The air introduced into the fermenter comes from a compressor 9 provided with a pre-filter 10, which filters out the larger particles suspended in the air, and a bacteriological filter 11 which must stop the smaller particles and contaminating agents. The ducts and apparatus located at the output of the still are at fairly high temperatures and are made of stainless steel, and their sterilization is effected by the steam furnished by a steam generator (not shown). It is in this manner that the containers, the preculture 7 and the supplement of nutritive solution 8 are also sterilized. The remainder of the ducts and the fermenter 6 are made of polyvinyl chloride and sterilized chemically by means of a solution of Javelle water prepared in a tank (not shown), which is caused to flow through the ducts and over the walls of the fermenter. The containers 12 and 13 hold hydrochloric acid solutions and silicones adapted to control the pH value and the formation of foam during the culture process. The apparatus indicated at the end of the treatment line are separating devices adapted to recover micro-organisms produced and may consist of a centrifugal separator 14 and a drum type filter 15.

Operation of the Successive Treating Stages

Once the various circuits and the fermenter have been sterilized, the residue from the first distillation is introduced into the fermenter 6. A pump 2 and a valve (not shown) properly supply the centrifugal separator 3 by adjusting the rate of flow to that which results in the most effective possible removal of yeast. The cooled liquid thus reaches the fermenter 6, which is then filled about four-fifths full. An anti-foaming agent is then added from the container 13 holding sterile silicones. The pH is adjusted by means of sterilized hydrochloric acid from the container 12. The addition of the anti-foaming agent and the control of the pH may be carried out throughout the culturing process as necessary. The air filtered through the filter 11 and coming from the compressor 9 is introduced into the fermenter 6 through the perforated ring 16. The flow of air is regulated in dependence upon requirements by a valve (not shown). At the same time the shaft carrying mixing blades 17, 18 is driven by the motor 19. The nutritive solution 8 may then be introduced into the fermenter 6 by a pump (not shown) and the broth is then innoculated with a pre-culture 7. During fermentation, the process is controlled by analysis and observation of specimens withdrawn at the level of a valve (not shown) located about halfway up the lateral wall of the fermenter. At the end of the culturing step the fermenter 6 is emptied by opening a valve (not shown) located at the lower part of the fermenter. The recovered biomass is then separated from the medium by separating devices such as a strip filter and the collected mycelium is incorporated in an animal feed.

EXAMPLE:

100 liters of residue is withdrawn from the first distillation step of a white wine distillery of the Cognac region. The characteristics of the medium are as follows:

| | |
|---|---|
| Temperature | 87° C |
| pH | 3.2 |
| Material in suspension | 3.2 g/liter |
| Chemical demand for oxygen | 36,400 mg of oxygen/liter |
| Biochemical demand for oxygen | 23,000 mg of oxygen/liter |
| Total dry materials in solution | 25.1 g/liter |
| Mineral materials | 2.8 g/liter |
| Organic materials | 22.3 g/liter |
| Total nitrogenous materials | 465 mg/liter |
| Reducing sugar | 1,470 mg/liter |
| Total sugar | 2,145 mg/liter |

The medium is centrifuged and a sludge recovered which, when dry, weighs 320 g, and consists essentially of the wine making yeasts of the raisin pulp. The medium from which the yeast has been removed is then cooled to 20–25° C in a sheet type heat exchanger and introduced in a sterile manner into the fermenter, which has already been sterilized. The medium is enriched by the introduction of a solution of sterilized urea at the rate of 1 g/liter of total medium (including the water in the solution). The pH is adjusted to 2 and the medium is agitated and aerated throughout the entire culture period. The material in the fermenter is then innoculated with a preculture formed in the same medium which has itself been innoculated with a suspension of lyophilized spores.

After 120 hours as a maximum the micro-organism is separated from its culture medium on a continuous strip filter. The mycelium which represents 9.800 kg by dry weight is recovered and contains 31% proteins. This mycelium will then be incorporated in an animal feed.

An analysis of the liquid phase indicates a chemical demand for oxygen of 6,300 mg of oxygen/liter and a biochemical demand for oxygen of 5,700 mg of oxygen/liter.

Consequently at this stage the depollution is not complete. The liquid medium is then filtered through a diatomaceous filter to remove the fine particles in suspension and then treated by reverse osmosis. This produces a completely depolluted liquid conforming to legislative requirements (a chemical demand for oxygen of less than 40 mg of oxygen/liter) which may be released into the environment, and a concentrated liquid containing organic materials which may be incorporated into animal feed.

The present invention has several advantages:

First, it makes possible to substantially decrease the pollution produced by distillery residues. In dependence upon the culture employed for the treatment of the residues of the distillery it makes it possible to obtain either protein which may be used as a protein supplement for an animal feed, or even human food, or molecules of micro-biological origin which in the two cases result in making the process for treating said residues less expensive. Moreover, this separating step prior to inoculation produces sludge consisting of wine making yeast, unicellular fungi and raisin pulps, which sludge is distinguished by its food-value from the produced biomass, which consists of the mycelium of filamentous pluricellular fungi.

What is claimed is:

1. Process for the treatment of residues from the distillation of white wines to produce protein feed which comprises the steps of dividing the residues into a sludge containing the wine making yeast and a clarified medium, cooling the clarified medium from which the yeasts have been removed until its temperature is between 20° and 25° C, innoculating said medium with a preculture produced by innoculating a like medium with a suspension containing a culture of a microorganism selected from the genus Penicillium, permitting said micro-organisms to develop in the medium while adjusting said medium to a pH of 1.5–5, separating and recovering the biomass produced from the culture medium, and treating the collected liquid after separation of the biomass to further purify it and recover the biosynthesized molecules which it contains.

2. The process of claim 1 in which the micro-organism is selected from the group consisting of Penicillium Spinulosum 129 (ATCC 20465), Penicillium Expansum 127 (ATCC 20466), Penicillium Commune 125 (ATCC 20464), Penicillium Commune 148, Penicillium Expansum 118, and Penicillium Frequentans 142.

3. The process of claim 1 in which the preculture is innoculated by means of a lyophilized suspension of spores.

4. The process of claim 1 in which the development of the micro-organism takes place under constant agitation and aeration.

5. The process of claim 4 in which the pH of the medium is adjusted to between 1.5 and 3.

6. The process of claim 1 in which the liquid is finally filtered through a diatomaceous filter and treated by reverse osmosis in order to obtain a purified water and a concentrate containing molecules bio-synthesized during the culture by the selected micro-organisms.

7. Animal food derived from the sludges obtained in the first step of the process of claim 1 after drying said sludges.

* * * * *